United States Patent
Nenadovic et al.

(10) Patent No.: US 10,475,716 B2
(45) Date of Patent: Nov. 12, 2019

(54) SENSOR SEMICONDUCTOR DEVICE AND METHOD OF PRODUCING A SENSOR SEMICONDUCTOR DEVICE

(71) Applicant: ams AG, Unterpremstaetten (AT)

(72) Inventors: Nebojsa Nenadovic, We Wijchen (NL); Agata Sakic, Eindhoven (NL); Micha In't Zandt, Veldhoven (NL); Frederik Willem Maurits Vanhelmont, Maaseik (BE); Hilco Suy, Rn Son en Breugel (NL); Roel Daamen, Herkenbosch (NL)

(73) Assignee: ams AG, Unterpremstaetten (AT)

( * ) Notice: Subject to any disclaimer, the term of this patent is extended or adjusted under 35 U.S.C. 154(b) by 0 days.

(21) Appl. No.: 15/775,792

(22) PCT Filed: Oct. 14, 2016

(86) PCT No.: PCT/EP2016/074787
§ 371 (c)(1),
(2) Date: May 11, 2018

(87) PCT Pub. No.: WO2017/084817
PCT Pub. Date: May 26, 2017

(65) Prior Publication Data
US 2018/0331007 A1    Nov. 15, 2018

(30) Foreign Application Priority Data
Nov. 16, 2015    (EP) .................. 15194745

(51) Int. Cl.
*H01L 23/31* (2006.01)
*G01N 27/12* (2006.01)
*H01L 23/00* (2006.01)

(52) U.S. Cl.
CPC ....... *H01L 23/3107* (2013.01); *G01N 27/121* (2013.01); *G01N 27/126* (2013.01); *H01L 24/48* (2013.01); *H01L 2224/04042* (2013.01); *H01L 2224/48091* (2013.01); *H01L 2224/48247* (2013.01); *H01L 2924/1815* (2013.01)

(58) Field of Classification Search
CPC ............... H01L 23/3107; H01L 24/48; H01L 2924/1815; H01L 2924/00014; H01L 2224/48247; H01L 2224/48091; H01L 2224/04042; G01N 27/126; G01N 27/121
See application file for complete search history.

(56) References Cited

U.S. PATENT DOCUMENTS

| 8,634,056 B2 * | 1/2014 | Streefkerk | G03F 7/2041 355/30 |
| 2007/0052429 A1 * | 3/2007 | Lindorfer | G01N 27/223 324/689 |

(Continued)

FOREIGN PATENT DOCUMENTS

| DE | 112013004203 T5 | 6/2015 |
| JP | 2002-162380 A | 6/2002 |

(Continued)

*Primary Examiner* — Yosef Gebreyesus
(74) *Attorney, Agent, or Firm* — Fish & Richardson P.C.

(57) ABSTRACT

The sensor semiconductor device comprises a substrate (1) with a main surface (2), a sensor region (3) on or above the main surface, a coating layer (4) above the main surface, and a trench (5) formed in the coating layer around the sensor region. The trench provides drainage of a liquid from the coating layer.

10 Claims, 1 Drawing Sheet

(56) References Cited

U.S. PATENT DOCUMENTS

| | | | |
|---|---|---|---|
| 2009/0243015 A1 | 10/2009 | Yoneda et al. | |
| 2010/0035373 A1 | 2/2010 | Hunziker et al. | |
| 2013/0069176 A1 | 3/2013 | Daamen et al. | |
| 2015/0279793 A1* | 10/2015 | Kuo | H01L 24/13 257/737 |

FOREIGN PATENT DOCUMENTS

| | | |
|---|---|---|
| JP | 2010-050452 A | 3/2010 |
| JP | 2012-068054 A | 4/2012 |

* cited by examiner

SENSOR SEMICONDUCTOR DEVICE AND METHOD OF PRODUCING A SENSOR SEMICONDUCTOR DEVICE

BACKGROUND OF THE INVENTION

Semiconductor devices are provided for various applications including sensors, in particular relative humidity sensors. A humidity sensor must be in contact with the environment and can thus be subject to condensation. Many sensor applications require fast recovery from condensation. Water droplets that are present on the sensor region should instantaneously vanish when the temperature rises above the dew point, which is the temperature at which the water vapor in a sample of air at constant barometric pressure condenses into liquid water at the same rate at which it evaporates.

US 2013/0069176 A1 discloses an integrated circuit package comprising a sensor element area covered with a protection layer. The integrated circuit is mounted on a carrier and connected by bond wires. An encapsulation covering the bond wires has an opening over the sensor element area. Inside the opening the protection layer comprises a channel surrounding the sensor element area.

JP 2010-050452 A discloses a method for manufacturing a sensor device with a plurality of chips arranged on a lead frame. A detector structure of the chips may comprise a polymer membrane of a humidity sensor. A buffer layer is formed above an integrated electronic circuit and leaves the detector structure free. A molded cover touches the buffer layer at the periphery of the detector structure, thus forming a sealed cavity above the detector structure.

JP 2012-068054 A discloses an electrostatic capacitance-type humidity sensor comprising a moisture-sensitive film surrounded by a hydrophilic film, which has a groove where condensed water forms a film. If the temperature of the air around the humidity sensor becomes higher than the dew-point temperature, the water in the groove part of the hydrophilic film evaporates, and dirt contained in the water remains.

US 2009/0243015 A1 discloses a method for manufacturing a semiconductor device wherein a resin layer is formed on an upper surface of a substrate including a photodiode such that the resin layer does not cover a light receiving region. Concentric grooves are formed in the resin layer so that the grooves surround the light receiving region. The photodiode is sealed with a molding resin. The grooves prevent molding resin from flowing into the light receiving region.

DE 112013004203 T5 discloses a sensor device comprising a moisture-sensitive layer, which is provided with a depression to prevent resin from entering a measurement portion during molding.

JP 2002-162380 A discloses a semiconductor ion sensor comprising a recessed portion around the ion sensing section. The recessed portion prevents inflow of resin into the ion sensing section.

SUMMARY OF THE INVENTION

The sensor semiconductor device comprises a substrate with a main surface, a sensor region on or above the main surface, a sensor element in the sensor region, a coating layer above the main surface, and a trench formed in the coating layer around the sensor region. The trench provides drainage of a liquid from the coating layer. The sensor element is completely covered by the coating layer, which is formed of a material that can be penetrated by moisture. The coating layer has an upper surface facing away from the substrate, the upper surface being plane in an area surrounded by the trench.

In an embodiment of the sensor semiconductor device, a hydrophilic liner is arranged in the trench. The hydrophilic liner may also be arranged between the main surface and the coating layer. The hydrophilic liner may be exposed in the trench.

In a further embodiment of the sensor semiconductor device, a channel is formed in the coating layer around the sensor region, so that the trench is arranged between the sensor region and the channel.

In a further embodiment of the sensor semiconductor device, a molding compound is arranged on or above the coating layer, so that the sensor region and the trench are not covered by the molding compound, and the channel completely surrounds an area that is entirely free from the molding compound.

In a further embodiment of the sensor semiconductor device, the area surrounded by the trench is entirely covered by the coating layer.

In a further embodiment of the sensor semiconductor device, the coating layer comprises a moisture sensitive material.

The method of producing a sensor semiconductor device comprises forming a coating layer encompassing a sensor region including a sensor element on or above a main surface of a substrate, and forming a trench in the coating layer around the sensor region, the trench providing drainage of a liquid from the coating layer. The sensor element is completely covered by the coating layer, which is formed of a material that can be penetrated by moisture. In an area surrounded by the trench, the coating layer is formed so that it has a plane upper surface facing away from the substrate.

In a variant of the method, a hydrophilic liner is arranged between the main surface and the coating layer, and the hydrophilic liner is exposed in the trench.

In a further variant of the method, a hydrophilic liner is arranged so that it is only present in the trench.

In a further variant of the method, the coating layer is formed from a moisture sensitive material.

In a further variant of the method, a channel is formed in the coating layer, the channel completely surrounding an area including the sensor region, so that the trench is arranged between the sensor region and the channel, a molding compound is applied on or above the coating layer, so that the sensor region and the trench are not covered by the molding compound, and the channel is used as a barrier to prevent the molding compound from extending into the area surrounded by the channel.

In a further variant of the method, the trench is formed completely surrounding an area that is entirely covered by the coating layer.

In the following, embodiments and variants of the invention are described in more detail in conjunction with the accompanying figures.

DETAILED DESCRIPTION

Figure 1:
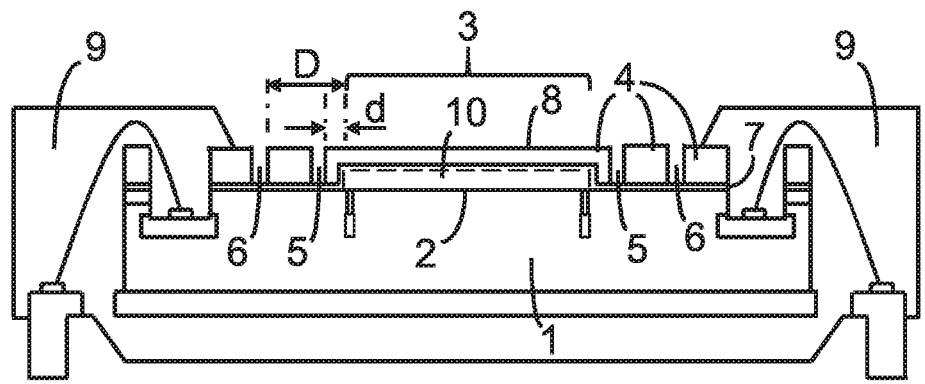
FIG. 1 is a cross section of an embodiment of the sensor semiconductor device.

FIG. 1 shows an integrated circuit package comprising the substrate 1 of the sensor semiconductor device, which comprises a sensor region 3 on or above an upper main surface 2. The substrate 1 may comprise a semiconductor body, which may include an integrated circuit like a CMOS circuit, for instance, and may be provided with a conventional wiring formed by metallization layers and intermetal dielectric.

A coating layer 4 is applied above the main surface 2. The coating layer 4 may be typically 4 to 5 μm thick, for example. The coating layer 4 can comprise organic or inorganic material. It may in particular comprise a polymer, for instance. The coating layer 4 may especially be provided as a sensitive layer. It may comprise a moisture sensitive material provided for a humidity sensor, especially a relative humidity sensor. Polyimide may be used for the coating layer 4, in particular as a moisture sensitive material.

A sensor element 10 may be arranged in the sensor region 3, as in the embodiment shown in FIG. 1 by way of example. The sensor element 10 may comprise a humidity sensor or an ambient light sensor, for instance, or another type of sensor. Details of the sensor element 10 are not relevant to the invention and are not shown in FIG. 1. If the sensor element 10 is provided, the coating layer 4 may cover the sensor element 10. If the sensor element 10 is provided for a humidity sensor and completely covered, the coating layer 4 is formed of a material that can be penetrated by moisture, such as polyimide, for instance.

The coating layer 4 may especially comprise a photo-definable layer, i. e., a layer that can be patterned by the use of photolithography, and may in particular comprise a photoresist. If the coating layer 4 does not comprise a photo-definable layer, a dedicated photoresist layer may be applied and patterned by standard photolithography to form a mask for etching the coating layer 4.

A trench 5 in the coating layer 4 is formed in the vicinity of the sensor region 3. The trench 5 may especially surround the sensor region 3, partially or completely. The trench 5 is provided to drain a liquid, especially water, which may condense on the surface of the coating layer 4, especially above the sensor region 3. The distance d between the sensor region 3 and the trench 5 may be smaller than 5 μm.

The trench 5 may completely surround the sensor region 3. In this case, the coating layer 4 may cover the entire area that is surrounded by the trench 5. In this area, the coating layer 4 may in particular comprise an essentially plane upper surface 8 as shown in FIG. 1.

A hydrophilic liner 7 may be arranged in the trench 5. It may be confined to the trench 5. Instead, the hydrophilic liner 7 may also be arranged between the main surface 2 and the coating layer 4, as shown in FIG. 1 by way of example. In the latter case, the hydrophilic liner 7 may be recessed in an area outside the trench 5, in particular in the sensor region 3. If a sensor element 10 is provided, the hydrophilic liner 7 may be arranged on or above the sensor element 10, as shown in FIG. 1 by way of example, or under the sensor element 10. If the hydrophilic liner 7 is provided, it helps to drain the liquid from the upper surface 8 of the coating layer 4 into the trench 5, especially if the hydrophilic liner 7 is exposed at the bottom of the trench 5.

A channel 6 may be formed around the sensor region 3 and around the trench 5. In some embodiments, the distance D between the sensor region 3 and the channel 6 may be at least three times as large as the distance d between the sensor region 3 and the trench 5. The channel 6 acts as a trap for a molding compound 9 that is used as encapsulation material. The advantage of the channel 6 for the molding process is explained in detail in US 2013/0069176 A1 cited above. The molding compound 9 can be provided to cover interconnects in the form of bond wires between an integrated circuit of the substrate 1 and a lead frame, on which the substrate 1 may be mounted. The lead frame provides external connections or terminals of the integrated circuit.

The molding compound 9 does not cover the sensor region 3 and the trench 5. In particular, the channel 6 may at least approximately delimit the area of an opening in the molding compound 9 where the upper surface 8 of the coating layer 4 may be bare to be sufficiently exposed to the environmental conditions.

If a sensor element 10 is provided, it may be arranged within the sensor region 3 on or above the main surface 2 of the substrate 1, as in the embodiment shown in FIG. 1 by way of example. It may especially be provided for a relative humidity sensor, whose operation is substantially improved by the fast recovery from condensation that is achieved with the trench 5. A sensor element may instead be embedded in the substrate 1, provided that the position is appropriate for the sensing operation.

Figure 2:
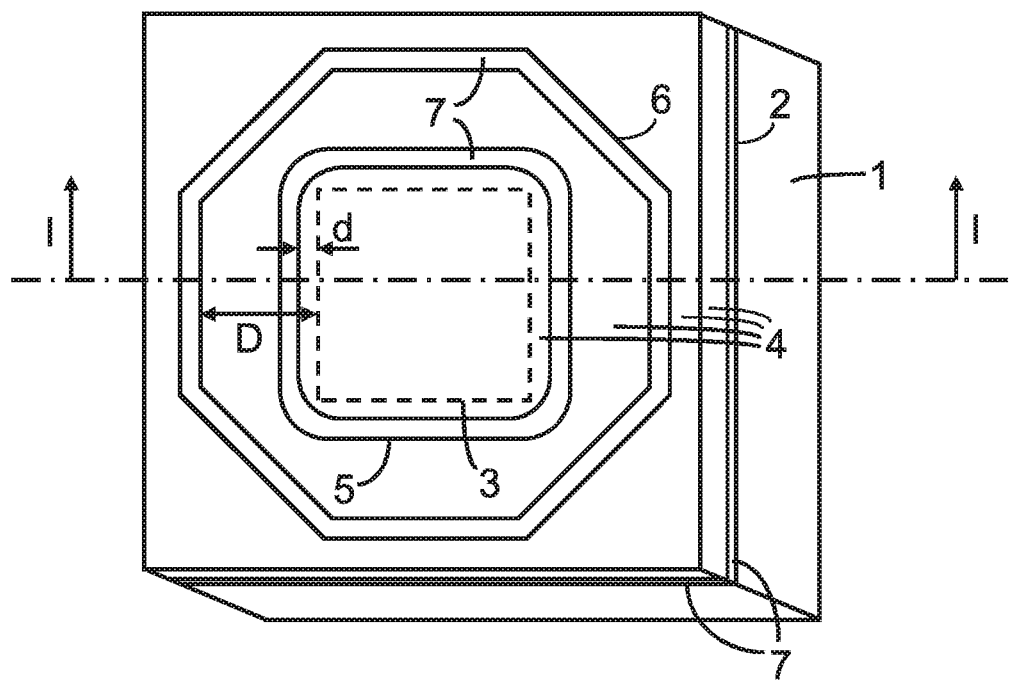
FIG. 2 is a top view of the embodiment shown in FIG. 1.

FIG. 2 is a top view of the embodiment according to FIG. 1. The position of the cross section of FIG. 1 is indicated in FIG. 2. The reference numerals of corresponding elements are the same in both figures. FIG. 2 shows the trench 5 completely surrounding the sensor region 3 at a small distance d. The trench 5 can thus be confined to the periphery of the sensor region 3 in view of an effective drainage. In the embodiment according to FIG. 2, the boundary of the sensor region 3 is a square, but it may have any other shape. The sensor region 3 may typically occupy an area of about $0.1 \times 0.1$ mm$^2$. If the trench 5 closely follows the boundary of the sensor region 3, it has essentially the same shape, as can be seen from FIG. 2. The trench 5 is arranged at locations where condensation is to be drained, but it is not necessary that the trench 5 completely surrounds the sensor region 3 and forms a closed path.

The channel 6 may be provided to block the molding compound 9, which is not shown in FIG. 2, from the area provided for the opening. For this purpose the shape of the channel 6 may be adapted to the outer limit of the opening, which may form an octagon, as shown in FIG. 2, or have any other suitable shape like a circle or a square, for instance. The channel 6 is arranged at a larger distance D from the sensor region 3 around the trench 5. In further embodiments, a minimum value of the distance D between the sensor region 3 and the channel 6 may be at least three times as large as a maximum value of the distance d between the sensor region 3 and the trench 5.

The trench 5 may be formed as a slit penetrating the coating layer 4. If a channel 6 is provided, it may also penetrate the coating layer 4. If such a slit completely surrounds the sensor region 3, the coating layer 4 is divided into separate portions, which are indicated in FIG. 2. If the hydrophilic liner 7 is provided, it is optionally exposed at the bottom of the trench 5 and may also be exposed at the bottom of the channel 6. This is also indicated in FIG. 2. The hydrophilic liner 7 attracts humidity and thus helps to drain liquid from the upper surface 8 of the coating layer 4.

If a photo-definable layer, like a photo-definable polymer, for instance, is used for the coating layer 4, it can be patterned by photolithography. If another material, like BCB (benzocyclobutene) for example, is applied to form the coating layer 4, the trench 5 can be etched into the coating layer 4. In this case, a photo-definable layer, like a photoresist for instance, may be applied and patterned for defining the trench 5.

The invention presents an improved way to enable fast recovery from condensation on sensors, in particular relative humidity sensors, by utilizing a slit or trench to collect condensed water. The trench is a passive element, which does not require electric operation and power consumption like an implemented heater. The formation of the trench is comparably easy and hence cheap. On the other hand it provides quick and effective drainage of liquid droplets.

The invention claimed is:

1. A sensor semiconductor device, comprising:
a substrate comprising a main surface;
a sensor region on or above the main surface;
a sensor element in the sensor region;
a coating layer above the main surface, the coating layer encompassing the sensor region;
the sensor element being completely covered by the coating layer;
the coating layer being formed of a material that can be penetrated by moisture;
a trench in the coating layer around the sensor region, the trench providing drainage of a liquid from the coating layer;
the coating layer having an upper surface facing away from the substrate, the upper surface being plane in an area surrounded by the trench; and
a hydrophilic liner arranged between the main surface and the coating layer, the hydrophilic liner being exposed in the trench.

2. The sensor semiconductor device according to claim 1, further comprising:
a channel formed in the coating layer around the sensor region, the trench being arranged between the sensor region and the channel.

3. The sensor semiconductor device according to claim 2, further comprising:
a molding compound being arranged on or above the coating layer;
the sensor region and the trench not being covered by the molding compound; and
the channel completely surrounding an area that is entirely free from the molding compound.

4. The sensor semiconductor device according to claim 1, wherein the area surrounded by the trench is entirely covered by the coating layer.

5. The sensor semiconductor device according to claim 1, wherein the coating layer comprises a moisture sensitive material.

6. A method of producing a sensor semiconductor device, comprising:
providing a hydrophilic liner;
forming a coating layer encompassing a sensor region including a sensor element on or above a main surface of a substrate,
the sensor element being completely covered by the coating layer,
the coating layer being formed of a material that can be penetrated by moisture, and
the hydrophilic liner being arranged between the main surface and the coating layer;
forming a trench in the coating layer around the sensor region, the trench providing drainage of a liquid from the coating layer;
in an area surrounded by the trench, forming the coating layer so that it has a plane upper surface facing away from the substrate; and
exposing the hydrophilic liner in the trench.

7. The method of producing a sensor semiconductor device according to claim 6, wherein
the coating layer is formed from a moisture sensitive material.

8. The method of producing a sensor semiconductor device according to claim 6, further comprising:
forming a channel in the coating layer, the channel completely surrounding an area including the sensor region, so that the trench is arranged between the sensor region and the channel;
applying a molding compound on or above the coating layer, so that the sensor region and the trench are not covered by the molding compound; and
using the channel as a barrier to prevent the molding compound from extending into the area surrounded by the channel.

9. The method of producing a sensor semiconductor device according to claim 6, wherein
the trench is formed completely surrounding an area that is entirely covered by the coating layer.

10. A sensor semiconductor device, comprising:
a substrate comprising a main surface;
a sensor region on or above the main surface;
a sensor element in the sensor region;
a coating layer above the main surface, the coating layer encompassing the sensor region;
the sensor element being completely covered by the coating layer;
the coating layer being formed of a material that can be penetrated by moisture;
a trench in the coating layer around the sensor region, the trench providing drainage of a liquid from the coating layer; and
a hydrophilic liner arranged between the main surface and the coating layer, the hydrophilic liner being exposed in the trench.

* * * * *